US009822396B2

(12) United States Patent
Litterst et al.

(10) Patent No.: US 9,822,396 B2
(45) Date of Patent: Nov. 21, 2017

(54) CHROMOSOME CONFORMATION CAPTURE IN PARTITIONS (71) Applicant: Bio-Rad Laboratories, Inc., Hercules, CA (US)

(72) Inventors: Claudia Litterst, Walnut Creek, CA (US); Svilen Tzonev, Pleasanton, CA (US); Jeremy Agresti, Richmond, CA (US)

(73) Assignees: Bio-Rad Laboratories, Inc.; Hercules, Inc.

( * ) Notice: Subject to any disclaimer, the term of this patent is extended or adjusted under 35 U.S.C. 154(b) by 242 days.

(21) Appl. No.: 14/622,515

(22) Filed: Feb. 13, 2015

(65) Prior Publication Data
US 2015/0225786 A1 Aug. 13, 2015

Related U.S. Application Data (60) Provisional application No. 61/939,565, filed on Feb. 13, 2014.

(51) Int. Cl.
*C12Q 1/68* (2006.01)

(52) U.S. Cl.
CPC .................. *C12Q 1/6809* (2013.01)

(58) Field of Classification Search
None
See application file for complete search history.

(56) References Cited

U.S. PATENT DOCUMENTS

| | | | |
|---|---|---|---|
| 5,210,015 | A | 5/1993 | Gelfand et al. |
| 5,538,848 | A | 7/1996 | Livak et al. |
| 5,863,736 | A | 1/1999 | Haaland |
| 2010/0173394 | A1 | 7/2010 | Colston, Jr. et al. |
| 2011/0092373 | A1 | 4/2011 | Colston, Jr. et al. |
| 2011/0092376 | A1 | 4/2011 | Colston, Jr. et al. |
| 2012/0124685 | A1* | 5/2012 | Henikoff ............ C12N 15/62 800/14 |
| 2013/0084574 | A1 | 4/2013 | Dong et al. |
| 2013/0123123 | A1 | 5/2013 | Chang et al. |
| 2013/0203605 | A1 | 8/2013 | Shendure et al. |
| 2014/0178889 | A1 | 6/2014 | Do et al. |

FOREIGN PATENT DOCUMENTS

| | | |
|---|---|---|
| WO | 2010/036352 A1 | 4/2010 |
| WO | 2010/151776 A2 | 12/2010 |

OTHER PUBLICATIONS

Gibson et al., "A novel method for real time quantitative RT-PCR", *Genome Research*, vol. 6, No. 10, pp. 995-1001 (1996).
Heid et al., "Real Time Quantitative PCR", *Genome Research*, vol. 6, pp. 986-994 (1996).
Holland et al., "Detection of specific polymerase chain reaction product by utilizing the 5'-3' exonuclease activity of Thermus aquaticus DNA polymerase", *Proc. Natl. Acad. Sci. USA*, vol. 4, No. 88, pp. 7276-7280 (1991).
Livak et al., "Oligonucleotides with Fluorescent Dyes at Opposite Ends Provide a Quenched Probe System Useful for Detecting PCR Product and Nucleic Acid Hybridization", *PCR Methods and Applications*, vol. 4, pp. 357-362 (1995).
McDermott et al., "Multiplexed target detection using DNA-binding dye chemistry in droplet digital PCR", *Anal. Chem.*, vol. 85, No. 23, pp. 11619-11627 (2013).
Shiroguchi et al., "Digital RNA sequencing minimizes sequence-dependent bias and amplification noise with optimized single-molecule barcodes", *PNAS*, vol. 109, No. 4, pp. 1347-1352 (2012).
Smith et al., "Highly-multiplexed barcode sequencing: an efficient method for parallel analysis of pooled samples", *Nucleic Acids Research*, vol. 13, e142 (2010).
Tyagi et al., "Molecular beacons: probes that fluoresce upon hybridization", *Nature Biotechnology*, vol. 14, pp. 303-308 (1996).
Tyagi et al., "Multicolor molecular beacons for allele discrimination", *Nat. Biotechnol.*, vol. 16, pp. 49-53 (1998).
Wilkie et al., "Purification of nuclei and preparation of nuclear envelopes from skeletal muscle", *Methods Mol Biol.*, vol. 463, pp. 23-41 (2008).
International Search Report and Written Opinion dated Jun. 17, 2015 for International Patent Application No. PCT/ US 2015/ 015934, 11 pages.
Ferraiuolo, et al., "From cells to chromatin: Capturing snapshots of genome organization with 5C technology", vol. 58, No. 3, Nov. 1, 2012, pp. 255-267.
Extended European Search Report from EP Appl. No. 15748616.8, dated Nov. 29, 2016.

* cited by examiner

*Primary Examiner* — David Thomas
(74) *Attorney, Agent, or Firm* — Kilpatrick Townsend & Stockton LLP (57) ABSTRACT

Methods compositions and kits are provided for performing a chromatin or chromosome conformation capture assay in partitions.

16 Claims, 4 Drawing Sheets

CHROMOSOME CONFORMATION CAPTURE IN PARTITIONS

CROSS-REFERENCE TO RELATED APPLICATION

This application claims priority to U.S. Provisional Application No. 61/939,565, filed, Feb. 13, 2014, the contents of which are hereby incorporated by reference in the entirety for all purposes.

BACKGROUND OF THE INVENTION

Techniques for studying the in vivo conformation of chromosomes can reveal a wealth of information regarding mechanisms of gene regulation. For example, chromosome conformation studies can reveal long-range regulatory control of genes by distal DNA sequence elements. One widely used methodology for determining the in vivo conformation of chromosomes is called chromosome conformation capture, or 3C. Other techniques extend 3C to provide further information or enable higher throughput analysis. Such techniques include, for example, 4C, 5C, 6C, Hi-C, ChIP-loop, and ChIA-PET.

Generally, chromosome conformation capture techniques involve a cross-linking step to fix the three-dimensional organization of chromatin, an endonuclease digestion step, a ligation step, and a reverse crosslinking step to generate a library of nucleic acid molecules. This library contains nucleic acid molecules in which sequence elements that were in proximity due to three-dimensional chromatin structure prior to the cross-linking event become proximal at the primary structural level after the reverse cross-linking event. Various amplification, sequencing, or other nucleic acid detection methods can then be utilized to identify the sequence elements that were proximal in three-dimensional space.

The ligation step can require extensive optimization to provide a suitable library of nucleic acid molecules. For example, intramolecular ligation events, in which cross-linked elements are ligated so that they exist on the same nucleic acid molecule, are generally favored. In contrast, it is generally desirable to avoid or minimize intermolecular ligation events, in which sequence elements that were not cross-linked become ligated. As another example, it can be important to ensure that no ligation occurs after reverse cross-linking. As yet another example, insufficient ligation can result in a library of molecules that provides little information.

BRIEF SUMMARY OF THE INVENTION

The present application provides an improved method for chromosome conformation capture using partitions. In some cases, the method does not require a ligation step. In some cases, the methods improve efficiency, completion, or fidelity of the ligation step, or a combination thereof.

In some embodiments, the present invention provides a method for detecting chromosomal DNA sequence elements that are in close proximity in a cell or in an intact nucleus comprising: a) cross-linking the chromosomal DNA in the cell or the intact nucleus, thereby forming a cross-linked DNA product in which chromosomal DNA sequence elements that are in close proximity in the cell are cross-linked; b) obtaining the cross-linked DNA product; c) digesting the cross-linked DNA product with an endonuclease to form a mixture containing a plurality of cross-linked DNA digest fragments; d) partitioning the cross-linked DNA digest fragments to create a plurality of partitions; and e) detecting the presence of two or more DNA sequence elements that are distal with respect to the primary sequence of the genome in a single partition, wherein detection of two or more DNA sequence elements in a single partition indicates that the two or more DNA sequence elements were in close proximity in the cell or intact nucleus.

In some embodiments, the present invention provides a method for detecting nucleic acid sequence elements that are in close proximity in a cell or in an intact nucleus comprising: a) cross-linking chromosomal DNA in the cell or the intact nucleus, thereby forming a cross-linked DNA product containing DNA and RNA, wherein nucleic acid sequence elements that are in close proximity in the cell are cross-linked; b) obtaining the cross-linked DNA product; c) digesting the cross-linked DNA product with an endonuclease to form a mixture containing a plurality of cross-linked DNA digest fragments; d) partitioning the cross-linked DNA digest fragments to create a plurality of partitions; and f) detecting the presence of two or more nucleic acid sequence elements that are distal with respect to the primary sequence of the genome in a single partition, wherein detection of two or more nucleic acid sequence elements in a single partition indicates that the two or more nucleic acid sequence elements were in close proximity in the cell or intact nucleus.

In some aspects, the cross-linked DNA digest fragments are partitioned such that the average number of cross-linked DNA digest fragments in each partition is about 1 or less. In some cases, the partitioning the cross-linked DNA digest fragments to create a plurality of partitions comprises creating at least 1,000, at least 10,000, at least 20,000, at least 100,000, or at least 1,000,000 partitions. In some cases, the partitions are less than about 100 nL, less than about 10 nL, or less than about 1 nL in volume.

In some aspects, the method further comprises reversing the cross-linking, thereby generating two reverse-cross-linked-DNA digest fragments from the cross-linked DNA digest fragment in the partitions. In some cases, the reversing the cross-linking is performed after the step of digesting the cross-linked DNA.

In some aspects, the detecting comprises detecting reverse-cross-linked DNA digest fragments in the partitions, wherein detection of two reverse-cross-linked DNA digest fragments in a single partition indicates that the two reverse-cross-linked DNA digest fragments were cross-linked, thereby detecting chromosomal DNA sequence elements that were in close proximity in the nucleus. In some cases, the reversing the cross-linking comprises heating the partitions to at least about 55° C., at least about 65° C., or at least about 95° C. In some cases, reversing the cross-linking comprises incubating the partitions with a proteinase, such as proteinase K.

In some aspects, the detecting comprises detecting in the partitions reverse-cross-linked DNA digest fragments that contain both DNA and RNA, wherein detection of two reverse-cross-linked DNA digest fragments in a single partition indicates that the two reverse-cross-linked DNA digest fragments were cross-linked, thereby detecting DNA and/or RNA sequence elements that were in close proximity in the nucleus. In some cases, the reversing the cross-linking comprises heating the partitions to at least about 55° C., at least about 65° C., or at least about 95° C. In some cases, reversing the cross-linking comprises incubating the partitions with a proteinase, such as proteinase K. In some cases, the detecting comprises reverse transcription.

In some aspects, all, substantially all, or a portion of the plurality of partitions contain a nucleic acid barcode. In some cases, the nucleic acid barcode is linked to a solid support.

In some aspects, detection comprises DNA amplification. In some cases, the DNA amplification comprises PCR. In some cases, the DNA amplification comprises targeted locus amplification (TLA). In some cases, the DNA amplification comprises reverse transcription or RT-PCR. In any of the foregoing embodiments, aspects, or cases, the detection step can comprise nucleic acid sequencing.

In some aspects, the cross-linking the chromosomal DNA in the intact nucleus comprises incubating a cell with a cross-linking agent. In some aspects, the cross-linking the chromosomal DNA in the intact nucleus comprises incubating a purified intact nucleus with a cross-linking agent.

In some embodiments, any of the foregoing methods can be performed on a plurality of intact nuclei or a plurality of cells containing intact nuclei. In some cases, the method further comprises quantitating the frequency of cross-linking of two or more nucleic acid (e.g., DNA) sequence elements, thereby quantitating the frequency that the two or more nucleic acid (e.g., DNA) sequence elements are in close proximity in the population of intact nuclei.

In some embodiments, the present invention provides a composition comprising a partition containing a cross-linked DNA digest fragment. In some embodiments, the present invention provides a composition comprising a partition containing a cross-linked DNA digest fragment that contains DNA and RNA. In some embodiments, the present invention provides a composition comprising a partition containing a reverse-cross-linked DNA digest fragment, wherein the reverse-cross-linked DNA digest fragment is a product of the process of cross-linking DNA in an intact nucleus, digesting the DNA with an endonuclease, forming a partition containing the digested and cross-linked DNA, and reversing the cross-linking. In some aspects, the partition contains a reverse cross-linked DNA digest fragment and reverse cross-linked RNA or cDNA. In some aspects, the partition further comprises a DNA amplification reagent or a nucleic acid sequencing reagent. In some cases, the DNA amplification reagent or nucleic acid sequencing reagent comprises an oligonucleotide primer or a DNA polymerase. In some cases, the composition further comprises at least 1,000; at least 10,000, at least 20,000, or at least 100,000 partitions. In some cases, the partitions are less than about 100 nL, less than about 10 nL, or less than about 1 nL in volume.

In some cases, the detecting the presence of two or more nucleic acid (e.g., DNA, cDNA, or RNA) sequence elements in a partition can include detecting such elements in a virtual partition. For example, detecting the presence of two or more nucleic acid sequence elements having the same barcode can indicate that the two or more nucleic acid sequence elements are in the same virtual partition and thus were in close proximity in the cell or intact nucleus. Alternatively, detecting in a partition can refer to detecting in a physical partition.

BRIEF DESCRIPTION OF DRAWINGS

FIG. 2 depicts an embodiment of a method of performing partition-based chromosome capture analysis. In this embodiment, double-stranded adaptor oligonucleotides are coupled to a solid support particle and partitioned. The adaptor oligonucleotides can contain a barcode that is unique for each solid support particle. The adaptor oligonucleotides can also contain one or more restriction sites, and primer binding sites for sequencing and/or amplification. Cross-linked DNA can be digested with a restriction enzyme and partitioned into the barcoded partitions. The adaptor oligonucleotides can be digested with a restriction enzyme (e.g., a thermostable restriction enzyme) to generate sticky ends that are compatible with one or more ends of the cross-linked DNA fragments, and ligated to the cross-linked DNA fragments. Partitions can be combined, and the DNA fragments optionally de-crosslinked, and amplified to generate amplicons. The amplicons can then be sequenced to analyze chromosome conformation.

FIG. 3 depicts an embodiment of a method of performing partitioned-based chromosome capture analysis. In this embodiment, single-stranded primer oligonucleotides are coupled to a solid support particle or incorporated in a gel support particle and partitioned. The primer oligonucleotides can contain a barcode that is unique for each solid support particle, and a hybridization region that can hybridize to cross-linked DNA. The hybridization region can be, e.g., a random hexamer as depicted. Cross-linked DNA can be digested with a restriction enzyme and partitioned into the barcoded partitions. The solid or gel support can be dissolved, e.g., by heating. The cross-linked DNA can be de-cross-linked and amplified by random priming from the single stranded primer oligonucleotide to generate amplicons. Partitions can then be combined. The amplicons can then be sequenced to analyze chromosome conformation.

DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the term "partitioning" or "partitioned" refers to separating a sample into a plurality of portions, or "partitions." Partitions can be solid or fluid. In some embodiments, a partition is a solid partition, e.g., a micro channel. In some embodiments, a partition is a fluid partition, e.g., a droplet. In some embodiments, a fluid partition (e.g., a droplet) is a mixture of immiscible fluids (e.g., water and oil), or an emulsion. In some embodiments, a fluid partition (e.g., a droplet) is an aqueous droplet that is surrounded by an immiscible carrier fluid (e.g., oil). In other embodiments, a fluid partition is an aqueous droplet that is physically or chemically separated from adjacent aqueous droplets such that the contents of one droplet does not diffuse into adjacent droplets.

The term "probe" refers to a molecule (e.g., a protein, nucleic acid, aptamer, etc.) that specifically interacts with or specifically binds to a target molecule. Non-limiting examples of molecules that specifically interact with or specifically bind to a target molecule include nucleic acids (e.g., oligonucleotides), proteins (e.g., antibodies, transcription factors, zinc finger proteins, non-antibody protein scaffolds, etc.), and aptamers.

The term "chromosome" refers to bacterial or eukaryotic chromosomes.

As used herein, chromosome structure includes primary, secondary, tertiary and quaternary structure. Primary chromosomal structure, or primary sequence, refers to the nucleotide sequence of the chromosome. Secondary structure can refer to higher levels of structural organization such as a double helix structure of double stranded DNA, the 11-nm fiber of double stranded chromosomal DNA bound to nucleosomes (e.g., beads on a string), or the 30-nm fiber of stacked and folded 11-nm fiber. Tertiary structure refers to the folding of the 30-nm fiber into loops, turns, pseudoknots, domains, or other tertiary structure elements. In some cases, tertiary chromosomal structure can bring DNA sequence elements that are distant in the primary sequence of the chromosome into close proximity. Quaternary structure refers to the intermolecular organization of two or more different chromosomes. In some cases, quaternary chromosomal structure can bring DNA sequence elements that are not physically linked into close proximity. As used herein, the term "chromatin" is used to refer to one or more chromosomes that are associated with protein or additional nucleic acids. For example, chromatin can be associated with histones, transcription factors, suppressors, enhances, polymerases, repair enzymes, methylases, demethylases, non-coding RNA molecules, and the like. As used herein, the term "chromosome" encompasses chromatin.

The term "proximity" when used in the context of the distance between two nucleic acid sequence elements in the nucleus refers to the distance in three-dimensional space between the two nucleic acid sequence elements. As such, DNA sequence elements in a chromosome that are close (e.g., within about 10, 50, 100, 150, 200, or 250 bp or more) in primary sequence are always in close proximity to each other. In some cases, DNA sequence elements that are distant in primary sequence in a chromosome (e.g., separated by more than about 200; 250; 300; 400; 500; 1000; 1500; 2000; 5000; 10,000; 25,000; 50,000; 100,000; 250,000; 500,000; or 1,000,000 bp) can be in close proximity to each other due to the tertiary or quaternary structure of the chromosome(s). In some cases, DNA sequence elements that lie on different chromosomes can be in close proximity to each other due to the quaternary structure of the chromosomes. In some cases, nucleic acid sequence elements are distal with respect to primary sequence because one or more elements are chromosomal DNA sequence elements and one or more other elements are RNA (or cDNA) sequence elements. As such, the nucleic acid sequence elements can be, or can be within, different nucleic acid molecules. In such cases, the two or more nucleic acid sequence elements can be in close proximity to each other due to their formation of a complex. For example, non-coding RNAs can associate with one or more DNA sequence elements in a genome.

A "DNA sequence element" refers to a double stranded or single stranded DNA sequence. In some embodiments, two or more DNA sequence elements (e.g., polynucleotides) detected in a partition indicate that the two DNA sequence elements existed in close proximity in a cell or cells from which the DNA sequence elements were obtained. In some cases, the DNA sequence element is a cDNA sequence. For example, the DNA sequence element can be a cDNA sequence generated by reverse transcription of an RNA.

The terms "label" and "detectable label" interchangeably refer to a composition detectable by spectroscopic, photochemical, biochemical, immunochemical, chemical, or other physical means. For example, useful labels include fluorescent dyes, luminescent agents, radioisotopes (e.g., $^{32}P$, $^{3}H$), electron-dense reagents, enzymes, biotin, digoxigenin, or haptens and proteins, nucleic acids, or other entities which can be made detectable, e.g., by incorporating a radiolabel into an oligonucleotide, peptide, or antibody specifically reactive with a target molecule. Any method known in the art for conjugating an antibody to the label can be employed, e.g., using methods described in Hermanson, *Bioconjugate Techniques* 1996, Academic Press, Inc., San Diego.

A molecule that is "linked" to a label (e.g., as for a labeled probe as described herein) is one that is bound, either covalently, through a linker or a chemical bond, or noncovalently, through ionic, van der Waals, electrostatic, or hydrogen bonds to a label such that the presence of the molecule can be detected by detecting the presence of the label bound to the molecule.

DETAILED DESCRIPTION OF THE INVENTION

I. Introduction

Described herein are methods, compositions, and kits for detecting chromosome or chromatin interactions between nucleic acid sequence elements. For example, methods, compositions, and kits are described for detecting chromosomal DNA sequence elements that are in close proximity in an intact nucleus. Such methods, compositions, and kits can, for example, be useful for detecting physiological and pathological alterations of the genome, analyzing epigenetic gene regulation, detecting the role of distal enhancer elements on gene expression, identifying DNA elements involved in DNA recombination, and determining the chromosome or chromatin structural requirements for stem cells or pluripotency. In some cases, the methods, compositions, and kits of the present invention can provide absolute or relative quantification of the frequency that two or more nucleic acid sequence elements in a cell or a population of cells are in proximity.

II. Methods

Described herein is a method for detecting chromosomal DNA sequence elements that are in close proximity in a cell or an intact nucleus comprising: a) cross-linking the chromosomal DNA in the cell or the intact nucleus, thereby forming a cross-linked DNA product in which chromosomal DNA sequence elements that are in close proximity in the cell are cross-linked; b) obtaining the cross-linked DNA product; c) digesting the cross-linked DNA product with an endonuclease to form a mixture containing a plurality of cross-linked DNA digest fragments; d) partitioning the cross-linked DNA digest fragments to create a plurality of partitions; and e) detecting the presence of two or more DNA sequence elements that are distal with respect to the primary sequence of the genome in a single partition, wherein detection of two or more DNA sequence elements in a single partition indicates that the two or more DNA sequence elements were in close proximity in the nucleus.

Also described herein is a method for detecting nucleic acid sequence elements that are in close proximity to one or more chromosomal DNA sequence elements in a cell or an intact nucleus comprising: a) cross-linking the chromosomal DNA in the cell or the intact nucleus, thereby forming a cross-linked nucleic acid product in which one or more chromosomal DNA sequence elements, and one or more RNA sequence elements, that are in close proximity in the cell are cross-linked; b) obtaining the cross-linked DNA product; c) digesting the cross-linked DNA product with an endonuclease to form a mixture containing a plurality of cross-linked DNA digest fragments; d) partitioning the cross-linked DNA digest fragments to create a plurality of partitions; and e) detecting the presence of two or more nucleic acid sequence elements that are distal with respect to the primary sequence of the genome in a single partition, wherein detection of two or more nucleic acid sequence elements in a single partition indicates that the two or more nucleic acid sequence elements were in close proximity in the nucleus.

a. Cross-Linking

As described herein, DNA can be cross-linked in a cell or an intact nucleus to form a cross-linked DNA product. In some cases, the DNA is cross-linked in a cell, or a plurality of cells. In other cases, one or more intact nuclei are obtained or provided, and the DNA is cross-linked therein. Methods and compositions for obtaining or providing intact nuclei are known in the art. See, e.g., Wilkie, et al., *Methods Mol Biol.* 2008; 463:23-41 and Blobel & Potter, *Science,* 1966; 154:3757:1662-1665.

The DNA can be cross-linked in the cell or the intact nucleus. In some cases, a reversible cross-linking agent and method is utilized. In other cases, a cross-linking agent or method is employed that results in irreversible cross-linking Exemplary cross-linking agents include, but are not limited to, formaldehyde, paraformaldehyde, formalin, other similar aldehydes, and other multi-functional (e.g., bi- or tri-functional) cross-linking reagents that can covalently cross-link protein-protein, DNA-DNA, RNA-RNA, RNA-DNA, protein-RNA, protein-DNA, or protein-RNA-DNA molecules together. In some cases, the cross-linking is performed with a cross-linking agent that reversibly cross-links primary protein amino groups (e.g., proteins bound to DNA) with other nitrogen atoms found on proximal protein or DNA molecules.

The cross-linking reagent can be applied at a suitable concentration. For example, the cross-linking reagent can be contacted with one or more cells or intact nuclei for approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 80, 90 minutes or longer. The concentration of cross-linking reagent contacted with the one or more cells or intact nuclei can be about 0.1, 0.2, 0.3, 0.4, 0.5, 0.6, 0.7, 0.9, 1.0, 1.2, 1.5, 2, 3, 4, or about 5%. In some cases, the cross-linking can be quenched after a suitable period of time to inhibit or stop the cross-linking reaction. Suitable quenching reagents include reagents containing one or more amines, e.g., one or more primary amines. Suitable quenching reagents further include, for example, methylamine, ethanolamine, Tris, dimethylamine, methylethanolamine, trimethylamine, aziridine, piperidiene, amiline, glycine, asparagine, arginine, and glutamine.

In some cases, the cross-linking conditions and the cross-linking agent are chosen such that only relatively intimate interactions are cross-linked. For example, a cross-linking agent can be selected that can bridge a distance of from about 1, 2, 3, 4, or 5 Å to about 6, 7, 8, 9, 10, 11, 12, 13, 14, 15, 16, 17, 18, 19, 20, 21, 22, 23, 24, or 25 Å. As another example, a cross-linking agent can be selected that can bridge a distance of about 2 Å, and/or less than about 3, 4, 5, 6, 7, 8, 9, 10, 11, 12, 13, 14, 15, 16, 17, 18, 19, 20, 21, 22, 23, 24, or 25 Å. As another example, a cross-linking agent can be selected that can bridge a distance of about, or of at least about, 2, 3, 4, 5, 6, 7, 8, 9, 10, 11, 12, 13, 14, 15, 16, 17, 18, 19, 20, 21, 22, 23, 24, or 25 Å.

In some cases, the cross-linking cross-links RNA molecules associated with chromosomal DNA or chromatin-associated proteins. Thus, cross-linked DNA product can contain DNA, RNA, protein, or a combination thereof. The cross-linked RNA molecules can be detected or quantified as described herein. For example, the cross-linked RNA molecules can be reverse transcribed and the resulting cDNA product can be detected. In some cases, the cross-linking cross-links RNA and DNA. In such cases, the cross-linked DNA product can contain RNA and DNA. The RNA and DNA molecules can be detected or quantified as described herein. For example, the RNA molecules can be reverse transcribed and the resulting cDNA product as well as the chromosomal DNA, or amplicons or fragments thereof, detected.

b. Digesting

The cross-linked chromosomal DNA product can be obtained or provided from the one or more cells or intact nuclei and then digested. Alternatively, the cross-linked DNA product in the one or more cells or intact nuclei can be digested, and the cross-linked and digested DNA fragments can then be obtained. Methods and compositions for digesting cross-linked DNA are known in the art. In some cases, the digestion is performed by contacting the cross-linked DNA product with an endonuclease. In some cases, a non-specific nuclease is utilized such as an endonuclease that cleaves any DNA sequence, or an endonuclease having a two, three, or four base pair recognition sequence. For example, the cross-linked DNA product can be digested with micrococcal nuclease, or DNAseI. Alternatively, the cross-linked DNA product can be digested with an endonuclease that cleaves a larger recognition sequence, such as a 5, 6, 7, 8 or more base pair recognition sequence. Exemplary endonucleases include, but are not limited to, Alu I, Apo I, Ase I, BamH I, BfuC I, Bgl II, BsaJ I, BstKT I, BstY I, Btg I, Cla I, CviKI-1, Dpn I, Dpn II, Eco47 III, EcoR I, EcoR V, EcoP15I, Fai I, Hae III, Hind III, Hpa II, HpyCH4 III, Kpn I, Mbo I, Mnl I, Mse I, Msp I, Nco I, Nde I, Nhe I, Not I, Pst I, Rsa I, Sac I, Sac II, Sal I, Sau3A I, Sfi I, Sma I, Taq I, Tsp509 I, Xba I, Xho I, or Xma I. As yet another alternative, the cross-linked DNA product can be sheared by physical means, such as by sonication, or by extrusion through a small orifice.

c. Purification

Cross-linked DNA product, before or after digestion or physical shearing, can be purified from one or more cells or intact nuclei. In some cases, the cross-linked DNA product, is purified from one or more of non-cross-linked DNA, non-cross-linked RNA, protein, cell debris, cell membrane, cross-linking agent, quenched cross-linking agent, or quenching agent. In some embodiments, the one or more cells or intact nuclei can be contacted with a detergent containing solution to obtain the cross-linked DNA product, or fragments of cross-linked DNA product. In some cases, the detergents include, but are not limited to, anionic detergents, cationic detergents, non-ionic detergents and zwitterionic detergents, or combinations thereof. Such combinations include: one or more cationic detergents with one or more anionic detergents; one or more cationic detergents with one or more non-ionic detergents; one or more cationic detergents with one or more zwitterionic detergents; one or more anionic detergents with one or more non-ionic detergents; one or more anionic detergents with one or more zwitterionic detergents; and one or more non-ionic detergents with one or more zwitterionic detergents. In some cases, one or more anionic detergents are combined with one or more non-ionic detergents. Non-limiting examples of anionic detergents include alkyl sulfates (e.g., sodium dodecylsulfate), alkyl sulfonates (e.g., octane sulfonic acid), bile salts, docusate sodium salt, and N-laurylsarcosine. Non-limiting examples of cationic detergents include bezalkonium chloride, cetyl pyridium chloride, dodecyltrimethylammonium chloride, Girard's reagent, and Hyamine® 1622. Non-limiting examples of non-ionic detergents include Tween®-20, Tween®-80, Triton® X-100, Triton® X-114, PEGylates, IGEPAL, Nonidet™-P40, Pluronic® F-68, Poloxamer 407, saponin and Tergitol®. Non-limiting examples of zwitterionic detergents include CHAPS, L-α-lysophosphatidyl choline, DDMAB, and miltefosine.

The cross-linked DNA product, can be further purified, or alternatively purified, before digestion or physical shearing, after digestion or physical shearing, or before and after digestion or physical shearing. Methods for purification of cross-linked DNA product, further include column purification, e.g., with an anion exchange resin, incubating the product with beads (e.g., magnetic beads) functionalized to bind nucleic acid, or the like.

d. Partitioning

After digestion or physical shearing, the fragments of cross-linked DNA product, resulting from digestion or shearing can be partitioned into a plurality of partitions. Partitions can include any of a number of types of partitions, including solid partitions (e.g., wells or tubes) and fluid partitions (e.g., aqueous droplets within an oil phase). In some embodiments, the partitions are droplets. In some embodiments, the partitions are micro channels. Methods and compositions for partitioning a sample are described, for example, in published patent applications WO 2010/036352, US 2010/0173394, US 2011/0092373, and US 2011/0092376, the entire content of each of which is incorporated by reference herein.

Fragments of cross-linked DNA product, can be partitioned into any number of partitions. In general, the number of partitions is chosen to ensure that a minority of, a substantial minority of, few, substantially no, or no partitions contain multiple cross-linked fragments. Thus, the presence of multiple DNA sequence elements in a single partition indicates that the two or more DNA sequence elements were present in the same cross-linked fragment. Similarly, the presence of one or more RNA and one or more DNA sequence elements in a single partition indicates that the sequence elements were present in the same cross-linked fragment. The number of partitions necessary to ensure adequate partitioning is dependent on a number of factors, including, but not limited to: (a) the size of the genome to be interrogated; (b) the method of digestion/shearing; (c) the number and size of cross-linked fragments (e.g., cross-linked DNA fragments) generated; (d) the desired resolution of the chromosome conformation capture analysis; and (e) the desired statistical significance. In general, the number of partitions is at least about 500; 1000; 10000; or 20,000; 30,000; 50,000; or more.

In some embodiments, reagents such as cross-linked product (e.g., digested or sheared cross-linked DNA, RNA, or DNA/RNA fragments), buffers, enzymes (e.g., polymerases for reverse transcription, amplification, barcoding, and/or sequencing), substrates, nucleotides, primers, salts, etc. are mixed together prior to partitioning, and then the sample is partitioned. In some cases, the reagents include a polymerase and the sample is partitioned shortly after mixing reagents together so that substantially all, or the majority, of polymerase activity occurs after partitioning. In other cases, the reagents are mixed at a temperature in which the polymerase proceeds slowly, or not at all, the sample is then partitioned, and the reaction temperature is adjusted to allow the polymerase reaction to proceed. For example, the reagents can be combined on ice, at less than 5° C., or at 0, 1, 2, 3, 4, 5, 6, 7, 8, 9, 10, 11, 12, 13, 14, 15, 16, 17, 18, 19, 20, 20-25, 25-30, or 30-35° C. or more. In general, one of skill in the art will know how to select a temperature at which one or more polymerase enzymes are not active. In some cases, a combination of temperature and time are utilized to avoid substantial polymerization prior to partitioning.

In some cases, reagents can be mixed using one or more hot start polymerase, such as a hot start DNA-dependent DNA polymerase or a host start RNA-dependent DNA polymerase. Thus, cross-linked product (e.g., digested or sheared cross-linked DNA, RNA, or DNA/RNA fragments), buffers, salts, nucleotides, labels, enzymes, etc. can be mixed and then partitioned. Subsequently, the polymerization reaction, including multiple rounds of polymerization, can be initiated by heating the partition mixtures to activate the one or more hot-start polymerases.

Additionally, reagents can be mixed together without one or more reagents necessary to initiate an enzymatic reaction (e.g., polymerization and/or amplification). The mixture can then be partitioned into a set of first partition mixtures and then the one or more essential reagents can be provided by fusing the set of first partition mixtures with a set of second partition mixtures that provide the essential reagent. Alternatively, the essential reagent can be added to the first partition mixtures without forming second partition mixtures. For example, the essential reagent can diffuse into the set of first partition mixture water-in-oil droplets. As another example, the missing reagent can be directed to a set of micro channels which contain the set of first partition mixtures.

In some embodiments, reagents can be mixed together to form a reaction mixture, and partitioned. Subsequently, one or more additional reagents can be added to the partitions. For example, one or more reagents can be injected into the partitions. In some cases, an electric field can be applied to an interface between a partition and a fluid to disrupt the interface and allow at least a portion of the fluid to enter the partition. As another example, one or more reagents can be directed to partitions in micro or nanoliter size wells via microfluidic techniques. Methods, compositions, and devices for injection of reagents into a partition can include, but are not limited to, those described in WO/2010/0151776.

Reagents that can be added by fusing partitions, injection, microfluidics or other means include but are not limited to reverse cross-linking reagents, reverse transcription reagents (e.g., a primer and/or RNA-dependent DNA polymerase), amplification reagents, detection reagents, sequencing reagents, ligation reagents, barcoding reagents, or combinations thereof. For example, protease (e.g., proteinase K) can be added into a partition to reverse cross-linking. As another example, DNA-dependent DNA polymerase (and, optionally, one or more primers) can be added into a partition to amplify the nucleic acid in the partition. As yet another example, barcodes, primers, ligase, polymerase, or combinations thereof can be added into a partition to barcode nucleic acid in the partition. In some cases, the barcodes are attached to, or otherwise incorporated in or associated with, a solid or gel support, and the solid or gel support with the barcodes—and optionally other barcoding reagents, such as primers, polymerase, ligase, or a combination thereof—are added to one or more partitions by fusion, injection, microfluidics, or other means.

As yet another example, reagents for sequencing of target DNA can be added into a partition. Such reagents can include but are not limited to nucleotides, or nucleotide analogues (e.g., detectably labeled nucleotides, terminator nucleotides, reversibly terminated nucleotides, or combinations thereof), polymerase, sulfurylase, luciferase, apyrase, or combinations thereof. As yet another example, detection reagents can be added into a partition. Such reagents can include, but are not limited to, intercalating dyes, detectably labeled nucleic acid probes and/or primers, molecular beacons, aptamers, or combinations thereof. As yet another example, reverse transcription reagents can be added into a partition. Such reagents can include reverse transcriptase and/or a reverse transcription primer (e.g., an oligodT primer, or a sequence specific primer). Reagents can be added into partitions (e.g., by injection, fusion, etc.) at multiple points. For example, cross-linked fragments can be added into barcoded partitions. Subsequently barcoding reagents can be added into the partitions. Subsequently, reverse transcription reagents can be added into the partitions.

In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes.

In some embodiments, the droplet is formed by flowing an oil phase through an aqueous sample comprising the DNA sequence elements to be detected. In some embodiments, the aqueous sample comprising the DNA sequence elements to be detected further comprises a buffered solution and two or more probes, or two or more pairs of probes, for detecting the DNA sequence elements.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, −20°, 0°, 3°, 4°, 5°, 6°, 7°, 8°, 9°, 10°, 15°, 20°, 25°, 30°, 35°, or 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

The microcapsule partitions can contain one or more probes (e.g., labeled probes as described herein) and can resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions can be incubated per mL. In some embodiments, the sample-probe incubations occur in a single well, e.g., a well of a microtiter plate, without inter-mixing between partitions. The microcapsules can also contain other components necessary for the incubation.

In some embodiments, the sample is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, the sample is partitioned into a sufficient number of partitions such that all, substantially all, or at least a majority of partitions have no more than 5 cross-linked DNA molecules (e.g., about 0.5, 1, 2, 3, 4, or 5 cross-linked DNA, RNA, or DNA/RNA molecules). In some embodiments, the sample is partitioned into a sufficient number of partitions such that all, substantially all, or at least a majority of partitions have no more than 1 cross-linked DNA molecule (e.g., about 0.05, 0.1, 0.2, 0.3, 0.4, 0.5, 0.75 or 1 cross-linked DNA, RNA, or DNA/RNA molecules). In some embodiments, on average no more than 5, 4, 3, 2, 1, 0.75, 0.5, 0.4, 0.3, 0.2, 0.1, or 0.05 cross-linked DNA, RNA, or DNA/RNA molecules are present in each partition. In some embodiments, on average about 0.05, 0.1, 0.2, 0.3, 0.4, 0.5, 0.75, 1, 2, 3, 4, or 5 cross-linked DNA, RNA, or DNA/RNA molecules are present in each partition. In some embodiments, in a population of partitions containing cross-linked DNA, RNA, or DNA/RNA molecules, the mode number of cross-linked DNA molecules in a partition is about 1 or 0.

In some embodiments, partitions contain excess detection reagents. For example, in some embodiments, partitions contain, on average, more than about 1 (e.g., 1, 2, 3, 4, 5, 6, 7, 8, 10, 12, 15, 20, 40, 50, 100, 150, 200, 250, 300, 350, 400, 500, 750, 1000 or more) primer, primer pair, or probe molecules for detection of target DNA sequence elements. In some embodiments, multiple detection reagents for detection of multiple target DNA sequence elements are present in the partitions. For example, 1, 2, 3, 4, 5, 6, 7, 8, 9, 10 or more different target DNA sequence elements can be detected in one or more partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

e. Detecting

In some embodiments, the presence or absence of two or more DNA sequence elements is detected in a partition, or a plurality of partitions. The presence of two or more DNA sequence elements in a single partition suggests that the two DNA sequence elements were in close physical proximity in the cell or intact nucleus from which it is derived. In some cases, the frequency with which DNA sequence elements are detected in a single partition indicates the frequency that the two sequence elements are in close physical proximity in the population of cells or intact nuclei from which the elements are derived.

In some embodiments, the presence or absence of an RNA sequence element is detected in a partition, or a plurality of partitions. In some cases, the presence or absence of an RNA sequence element and one or more DNA sequence elements in a single partition suggests that the two or more sequence elements were in close physical proximity in the cell or intact nucleus from which it is derived. In some cases, the frequency with which RNA and, optionally one or more DNA sequence elements, are detected in a single partition indicates the frequency that the two or more sequence elements are in close physical proximity in the population of cells or intact nuclei from which the elements are derived. The RNA sequence elements can be reverse transcribed into corresponding complementary DNA sequence elements and then detected using any of the DNA detection methods described herein.

In some cases, the RNA sequence elements are non-coding RNA sequence elements, or a fragment thereof. For example, described herein are methods, compositions, and kits for detection of a physical association of one or more non-coding RNA sequence elements with one or more chromosomal DNA sequence elements. Non-coding RNA sequence elements include, but are not limited to, microRNAs, Y-RNAs, riboswitches, piwi-interacting RNAs, CRISPR/Cas guide RNAs, telomerase RNA, X-inactive-specific transcript, antisense RNAs, long non-coding RNAs, small nucleolar RNAs, and the like.

Methods for detecting DNA sequence elements are known in the art and include, but are not limited to hybridization of probes or primers, sequencing, and/or amplification. In some embodiments, cross-linked DNA products, or fragments thereof (e.g., fragments from digestion or shearing) can be amplified. In some cases, DNA sequence elements, or portion thereof, can be amplified. In some cases, the DNA can be amplified before partitioning, within the partition, or after partitions are combined. In some cases, the DNA can be amplified as a means of detection, or as a means of barcoding. In some cases, amplification is performed in combination with one or more of ligation, reverse cross-linking, barcoding, detecting, sequencing, cross-linking, or digestion or shearing.

More generally, the amplification methods described herein are useful for amplifying the amount of cross-linked DNA products, fragments thereof, or DNA sequence elements therein. Amplification can be before and/or after cross-linking, digesting or shearing, reverse cross-linking, ligating, detecting, or barcoding. Methods for DNA amplification are well known in the art and include polymerase chain reaction (PCR), the ligase chain reaction (LCR), the transcription based amplification system (TAS), nucleic acid sequence-based amplification (NASBA), strand displacement amplification (SDA), rolling circle amplification (RCA), loop-mediated isothermal amplification (LAMP), and hyper-branched RCA (HRCA). In some cases, the PCR can be endpoint PCR, real-time PCR, qPCR or digital PCR (e.g., digital droplet PCR).

In some cases, one or more DNA sequence elements can be amplified by targeted locus amplification (TLA). TLA uses the physical proximity of nucleotides within a locus of interest as the basis of selection. DNA is cross-linked, and digested. In some cases, the cross-linked and digested DNA is re-ligated. A small locus specific primer is then used to amplify tens of thousands of surrounding base pairs. In this manner, the complete sequence of a locus can be amplified regardless of its nucleotide composition. Amplified loci can in turn be sequenced, e.g., with Next Generation Sequencing technologies. In some cases, multiple small locus specific primers are used to perform TLA on multiple loci.

Amplification can utilize one or more primers. In some cases, one or more of the amplification primers is the same as the barcode adaptor primer. In some embodiments, amplification is performed in a complex mixture rather than in a set of partition mixtures. For example, cross-linked DNA, RNA, or DNA/RNA fragments can be barcoded in a set of partitions, the partitions can then be combined and then amplified. In some cases, the use of a barcode sequence or label on the first or second strand synthesis primer can allow one practicing the invention to determine which partition mixture an amplification reaction product derived from. Thus, although partitions are not necessarily kept physically intact, they are maintained.

In other embodiments, the amplification is performed in the same partitions in which digestion, barcoding, reverse cross-linking, and/or reverse-transcription, and/or ligation, or combinations thereof, are performed. Amplification reagents can be added to the partitions by droplet fusion, micro channel flow, diffusion, or a combination thereof. In yet other embodiments, digestion, barcoding, reverse cross-linking, and/or reverse transcription, and/or ligation can be performed in a set of partition mixtures, the products can be recovered, and then amplification performed in a second set of partition mixtures.

In some embodiments, the partitions are analyzed by DNA sequencing methods including, but not limited to, fragment analysis, dideoxy sequencing (e.g., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

A digital readout assay, e.g., digital analysis, can be used to count the frequency that a particular DNA sequence element is in proximity to one or more other DNA sequence elements. The frequency can be determined by detecting the number of times a cross-linked DNA, RNA, or DNA/RNA fragment containing the DNA (e.g., DNA or cDNA) sequence element is cross-linked to one or more different fragments containing the other DNA (e.g., DNA or cDNA) sequence element(s). This can be determined by partitioning the cross-linked products or fragments thereof and identifying the partitions containing the two or more DNA (e.g., DNA or cDNA) sequence elements. Generally, the process of digital analysis involves determining for one or more partitions of a sample whether the partition is positive or negative for the presence of the DNA (e.g., DNA or cDNA) sequence element(s) to be detected.

In some embodiments, a partition is "positive" for the presence of the DNA (e.g., DNA or cDNA) sequence element if an amplified target nucleic acid is detected in the partition. In some embodiments, the amplified target nucleic acid is detected by detecting the presence of a signal generated by a label linked to a probe (e.g., a fluorescent, chemiluminescent, radioactive, or enzymatic label linked to a probe, such as an oligonucleotide, protein, peptide, or an aptamer probe). In some embodiments, two or more probes are detected in the partition by detecting the production of a signal that is generated when two labeled probes are present in the same partition but not in the absence of one or both probes from the same partition. In some embodiments, partition is "negative" for the presence of the target molecule if no amplified target nucleic acid is detected.

In some embodiments, the method of detection comprises fluorescence detection. Methods of detecting accumulated amplification product using fluorescence are well known in the art. Examples of suitable approaches include, for example the use of use of intercalating dye, the use of labeled probes in conjunction with 5' nuclease cleavage, and the use of structured probes.

The use of intercalating dyes utilizes fluorogenic compounds that only bind to double stranded DNA. In this type of approach, amplification product (which in some cases is double stranded) binds dye molecules in solution to form a complex. With the appropriate dyes, it is possible to distinguish between dye molecules remaining free in solution and dye molecules bound to amplification product. For example, certain dyes fluoresce efficiently only when bound to double stranded DNA, such as reverse transcription and/or amplification product. Examples of such dyes include, but are not limited to, SYBR Green and Pico Green (from Molecular Probes, Inc., Eugene, Oreg.), ethidium bromide, propidium iodide, chromomycin, acridine orange, Hoechst 33258, TOTO-I, YOYO-1, and DAPI (4',6-diamidino-2-phenylindole hydrochloride). Additional description regarding the use of intercalation dyes is provided, e.g., by Zhu et al., *Anal. Chem.* 66:1941-1948 (1994).

In some embodiments, the intercalating dyes can be used to discriminate between non-target containing, single positive, and double positive partitions. In some cases, intercalating dyes can be used to discriminate between single positive, double-positive, and multiply positive partitions (e.g., positive for 3, 4, 5, or more structurally different target sequences or amplicons thereof). For example, in some cases, partitions containing 2 or more target sequences, and an intercalating dye that detects the target sequences or amplicons thereof, can provide a greater detectable signal than partitions containing only one target sequence or amplicon thereof. Similarly partitions containing only 1 target sequence or amplicon thereof, and an intercalating dye, can provide a higher detectable signal than partitions containing no target sequence or amplicon thereof. As yet another example, the concentrations of primers for amplification of specific target sequences can be varied to alter the amount of amplicon generated in an end-point amplification (e.g., PCR or RT-PCR) reaction. Thus, the detection with an intercalating dye can distinguish between the presence or absence of different target sequence amplicons on the basis of signal intensity. Methods, compositions, and devices for multiplex detection of target sequences, reverse transcripts, and/or amplicons thereof, can be found, e.g., in McDermott, et al. Anal. Chem., 2013, 85 (23), pp 11619-11627; and US/2014/0178889.

Fluorogenic nuclease assays are another example of a product quantification method that can be used successfully with the devices and methods described herein. The basis for this method of monitoring the formation of amplification product is to measure amplicon accumulation using a dual-labeled fluorogenic oligonucleotide probe, an approach frequently referred to in the literature as the "TaqMan" method.

The probe used in such assays can be a short (e.g., approximately 20-25 bases in length) polynucleotide that is labeled with two different fluorescent dyes. In some cases, the 5' terminus of the probe can be attached to a reporter dye and the 3' terminus attached to a quenching moiety. In other cases, the dyes can be attached at other locations on the probe. The probe can be designed to have at least substantial sequence complementarity with the probe-binding site on the target nucleic acid. Upstream and downstream PCR primers that bind to regions that flank the probe binding site can also be included in the reaction mixture. When the fluorogenic probe is intact, energy transfer between the fluorophore and quencher moiety occurs and quenches emission from the fluorophore. During the extension phase of PCR, the probe is cleaved, e.g., by the 5' nuclease activity of a nucleic acid polymerase such as Taq polymerase, or by a separately provided nuclease activity that cleaves bound probe, thereby separating the fluorophore and quencher moieties. This results in an increase of reporter emission intensity that can be measured by an appropriate detector. Additional details regarding fluorogenic methods for detecting PCR products are described, for example, in U.S. Pat. No. 5,210,015 to Gelfand, U.S. Pat. No. 5,538,848 to Livak, et al., and U.S. Pat. No. 5,863,736 to Haaland, each of which is incorporated by reference in its entirety, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 4 88:7276-7280, (1991); and Livak, K. J., et al., PCR Methods and Applications 357-362 (1995).

Structured probes (e.g., "molecular beacons") provide another method of detecting accumulated amplification product. With molecular beacons, a change in conformation of the probe as it hybridizes to a complementary region of the amplified product results in the formation of a detectable signal. In addition to the target-specific portion, the probe includes additional sections, generally one section at the 5' end and another section at the 3' end, that are complementary to each other. One end section is typically attached to a reporter dye and the other end section is usually attached to a quencher dye. In solution, the two end sections can hybridize with each other to form a stem loop structure. In this conformation, the reporter dye and quencher are in sufficiently close proximity that fluorescence from the reporter dye is effectively quenched by the quencher. Hybridized probe, in contrast, results in a linearized conformation in which the extent of quenching is decreased. Thus, by monitoring emission changes for the reporter dye, it is possible to indirectly monitor the formation of amplification product. Probes of this type and methods of their use is described further, for example, by Piatek, A. S., et al., Nat. Biotechnol. 16:359-63 (1998); Tyagi, S. and Kramer, F. R., Nature Biotechnology 14:303-308 (1996); and Tyagi, S. et al., Nat. Biotechnol. 16:49-53 (1998).

In some embodiments, a detector that is capable of detecting a signal or multiple signals is used to analyze each partition for the presence or absence of the target molecule. For example, in some embodiments a one or two-color reader (fluorescence detector) is used. The fraction of positive-counted partitions can enable the determination of absolute concentrations, or relative concentrations, for the DNA sequence elements to be detected. In some cases, the fraction of positive-counted partitions can enable the determination of the relative or absolute frequency with which a DNA (e.g., DNA or cDNA) sequence element interacts with one or more other DNA sequence element(s).

Once a binary "yes-no" result has been determined for each of the partitions of the sample, the data for the partitions is analyzed using an algorithm based on Poisson statistics to quantify the amount of target molecule in the sample. Statistical methods for quantifying the concentration or amount of a target molecule or target molecules is described, for example, in WO 2010/036352, which is incorporated by reference herein in its entirety.

f. Reverse-Crosslinking

In some embodiments, the cross-linked DNA, RNA, or DNA/RNA fragments (e.g., digested or sheared), is reverse cross-linked. For example, the cross-linked fragments can be reverse cross-linked to allow reverse transcription, amplification, sequencing, and/or detection by hybridization of a nucleic acid probe. In some cases, the reverse cross-linking is performed in the partitions. In some cases, cross-linked nucleic acid is digested or sheared, partitioned, then reverse cross-linked before detection. In other cases, cross-linked nucleic acid is partitioned, digested or sheared, then reverse cross-linked before detection. In still other cases, cross-linked nucleic acid is partitioned and digested or sheared (e.g., in either order), and then detected without reverse cross-linking.

Reverse cross-linking can be performed after partitioning. As used herein, reverse-crosslinking, de-crosslinking, or the like, refers to treating a cross-linked nucleic acid fragment, or set of cross-linked nucleic acid fragments, to remove one or more, or substantially all, or all DNA:DNA, DNA:RNA, RNA:protein, DNA:protein, or RNA:DNA:protein cross-links that were added during the cross-linking. For example, cross-linked nucleic acid can be partitioned, then reverse cross-linked. In some cases, the partitioned cross-linked nucleic acid is barcoded (e.g., by ligation or polymerization) and then reverse cross-linked. In some cases, the partitioned cross-linked nucleic acid is reverse cross-linked and then barcoded (e.g., by ligation or polymerization). In some cases, the partitioned cross-linked nucleic acid is reverse cross-linked and then amplified. In some cases, the partitioned cross-linked nucleic acid is reverse cross-linked after being subjected to one or more of the following, or a combination thereof: reverse transcription, amplification, sequencing, polymerization, ligation, barcoding, probe hybridization, or combining of partitions. In some cases, the partitioned cross-linked nucleic acid is reverse cross-linked before being subjected to one or more of the following, or a combination thereof: reverse transcription, amplification, sequencing, polymerization, ligation, barcoding, probe hybridization, or combining of partitions.

Reverse cross-linking can be performed as desired. In some cases, the reverse cross-linking can be performed by contacting the cross-linked nucleic acid fragments with a protease. Exemplary proteases include, but are not limited to, serine proteases, such as Proteinase K, chymotrypsin, trypsin, elastin, subtilisin; threonine proteases; cysteine proteases, such as caspase, cathepsins, papain; aspartate proteases, such as rennin, chymosin, cathepsin D, pepsin; metalloproteases, such as aminopeptidase, dipeptidylpeptidase, angiotensin converting enzyme, carboxypeptidase; and glutamic acid peptidases. In some cases, the protease is Proteinase K. In some cases, the cross-linked DNA fragments are contacted with the protease for at least about 5, 10, 15, 20, 25, 30, 35, 40, 50, 60, 75, 90, 100, 120, or 200 minutes.

In some cases, the reverse cross-linking is performed by heating the cross-linked nucleic acid fragments. In some cases, the cross-linked nucleic acid fragments are reverse cross-linked by heating the partitions, containing the cross-linked nucleic acid fragments, to at least about 55° C., at least about 65° C., or at least about 95° C. for at least about 5, 10, 15, 20, 30, 60, 90, 100, 120, 180, 200, 240, 300, 360, 400, 500, 600, 720, 800, 900, 1000, 1500, 2000, or 4000 seconds or more. In some cases, the cross-linked nucleic acid fragments are reverse cross-linked by contacting the cross-linked nucleic acid fragments with a protease and incubating the partitions containing the cross-linked nucleic acid fragments at a temperature at which the protease is active. For example, partitions can be contacted with proteinase K and incubated at from about 20° C. to about 65° C. for at leat about 5, 10, 15, 20, 30, 60, 90, 100, 120, 180, 200, 240, 300, 360, 400, 500, 600, 720, 800, 900, 1000, 1500, 2000, or 4000 seconds or more. In some cases, the cross-linked nucleic acid fragments are reverse cross-linked by contacting the cross-linked DNA fragments with a protease, incubating at one or more of the foregoing protease contact times, and then inactivating the protease by heating at one or more of the foregoing heating times or temperatures. Additionally, or in the alterative, protease denaturants or inhibitors can be used to control the protease activity.

In some cases, a high salt buffer can be used to reverse cross-link nucleic acid. In some cases, the high salt buffer in combination with heating and/or proteinase treatment can reverse cross-link nucleic acid. Exemplary high salt buffers include, but are not limited to 500 mM to 1 M NaCl. Proteinase digestion, heating, and high salt buffers can be applied in any combination, whether simultaneously or sequentially to achieve reverse cross-linked nucleic acid.

g. Ligating

In some embodiments, the cross-linked nucleic acid products, or fragments thereof are ligated. For example, the cross-linked nucleic acid products, or fragments thereof, can be ligated to add adaptor polynucleotides. In some cases, the adaptor polynucleotides can be used to perform detection (e.g., amplification and/or sequencing) or to barcode the cross-linked nucleic acid products, or fragments thereof. In some cases, ligation is performed in the partitions. In some cases, ligation is performed before partitioning. In some cases, ligation is performed after partitions are combined. In some cases, the ligation is performed after reverse transcription. In some cases, ligation is not performed. For example, partitioning can be used to maintain physical proximity of cross-linked nucleic acid products, amplicons, reverse transcripts, or fragments thereof, during downstream processing and/or detection without the need for ligation. As another example, cross-linked nucleic acid can be partitioned, then barcoded (e.g., by ligation or polymerization), and the partitions combined. The barcodes can then be used to maintain virtual partitioning and/or virtual cross-linking of nucleic acid products, reverse transcripts, or fragments or amplicons thereof, during downstream processing and/or detection. Therefore, detecting the presence of two or more nucleic acid sequence elements in a partition, can include detecting of such sequence elements, or fragments or amplicons thereof, in a virtual partition. In some cases, partitioned cross-linked nucleic acid can be reverse cross-linked before or after partitions are combined, or before or after ligating or barcoding.

Ligation methods suitable for the methods described herein are known in the art. In some cases, the ligation is performed with a ligase that is specific for ligating together two double-stranded DNA molecules. In some cases, the ligation requires or is greatly facilitated by the presence of complementary single-stranded sticky ends on the DNA ligation reactants. In some cases, the ligation is performed with one or more of the following ligases: T4 DNA ligase, Tfi DNA ligase, DNA ligase I, DNA ligase II, DNA ligase III, DNA ligase IV, or a small footprint DNA ligase.

In some cases, ligation is performed to physically link cross-linked DNA fragments prior to reverse cross-linking. In some cases, ligation is performed to incorporate adaptor oligonucleotides containing a barcode, a sequencing primer binding site, an amplification primer binding site, and/or a detectable label. In some cases, ligation is performed to prepare a 5C or Hi-C library.

In some cases, adaptors may be phosphorylated in order to facilitate the ligation. Kinases useful for phosphorylating polynucleotides include, but are not limited to, T7 polynucleotide kinase and T4 polynucleotide kinase (PNK).

In other embodiments, nick-translation with, for example, E. coli DNA polymerase I, is carried out instead of phosphorylation and ligation of adaptors. In nick translation, free 3'-hydroxyl groups are created within the DNA by "nicks" caused by DNase I treatment or by the free 3' —OH groups resulting from the adaptors. DNA polymerase I then catalyzes the addition of a nucleotide (labeled or unlabeled) to the 3'-hydroxyl terminus of the nick. At the same time, the 5'-to-3' exonuclease activity of this enzyme eliminates the nucleotide unit from the 5'-phosphoryl terminus of the nick. A new nucleotide with a free 3' —OH group is incorporated at the position of the original excised nucleotide unit in the 3' direction.

h. Barcoding

In some embodiments, the partitioned cross-linked nucleic acid fragments, or amplicons or reverse transcripts thereof, are barcoded. Barcoding allows the maintenance of virtual partitioning even after partitions have been physically combined. Therefore, detecting the presence of two or more nucleic acid sequence elements in a partition, can include detecting of such sequence elements, or fragments or amplicons thereof, in a virtual partition. For example, detecting the presence of two or more nucleic acid sequence elements having the same barcode can indicate that the two or more nucleic acid sequence elements are in a virtual partition, and thus were in close proximity in the cell or intact nucleus.

As used herein a "barcode" is a short nucleotide sequence (e.g., at least about 4, 6, 8, 10, 12, 14, or 16, nucleotides long) that uniquely defines a nucleic acid molecule, a set of nucleic acid molecules (e.g., a set of DNA molecules from a particular partition), or a polymerization product, or set of products, generated in a particular partition. For example, partitioned cross-linked nucleic acid (e.g., DNA) fragments can be hybridized to a primer, or set of primers. The primer(s) in each partition can contain a different barcode sequence. Template directed polymerization from the hybridized primer(s) can then be performed, thus incorporating a unique barcode into the polymerization product(s) of each partition. Partitions can then be combined, and optionally amplified, without losing track of which partitions contained which cross-linked nucleic acid fragment or product(s) polymerized therefrom. Thus, presence or absence of polymerization product(s) or cross-linked nucleic acid fragment comprising each barcode can be counted (e.g. by sequencing, hybridization, etc.) without the necessity of maintaining physical partitions.

The length of the barcode sequence determines how many unique samples can be differentiated. For example, a 4 nucleotide barcode can differentiate $4^4$ or 256 samples or less, a 6 nucleotide barcode can differentiate 4096 different samples or less, and an 8 nucleotide barcode can index 65,536 different samples or less. Additionally, barcodes can be attached to both strands of a double stranded molecule either through barcoded primers for both first and second strand synthesis or through ligation. The use of two different barcodes on the two strands increases the number of independent events that can be distinguished. Alternatively, the same barcode can be attached to both strands of a double stranded molecule. The use of the same barcode can result in identical barcodes on both strands. The dual barcoding can provide a check against subsequent detection errors such as sequencing or amplification errors confounding downstream analysis and allow detection of either or both strands without compromising quantification. The use of barcode technology is well known in the art, see for example Katsuyuki Shiroguchi, et al. *Digital RNA sequencing minimizes sequence-dependent bias and amplification noise with optimized single-molecule barcodes*, PNAS (2012); and Smith, A M et al. *Highly-multiplexed barcode sequencing: an efficient method for parallel analysis of pooled samples*, Nucleic Acids Research Can 11, (2010).

In some cases, cross-linked nucleic acid fragments can be partitioned such that each partition contains about 1 or fewer cross-linked nucleic acid fragments, reverse cross-linked, the reverse cross-linked products barcoded, and then the partitions combined (e.g., the emulsion broken). As another example, cross-linked nucleic acid fragments can be partitioned such that each partition contains about 1 or fewer cross-linked nucleic acid fragments, the cross-linked nucleic acid fragments barcoded, reverse cross-linked, and then the partitions combined (e.g., the emulsion broken). As yet another example, cross-linked nucleic acid fragments can be partitioned, the cross-linked nucleic acid fragments barcoded, the partitions combined (e.g., the emulsion broken), and the barcoded and cross-linked nucleic acid fragments reverse cross-linked. In some cases, the barcoded fragments allow subsequent detection steps to identify which nucleic acid sequence elements were present in the same partition. In some cases, the cross-linked nucleic acid fragments are partitioned into partitions containing barcodes (e.g., barcodes linked to, or incorporated into, a solid or gel support). In some cases, the cross-linked nucleic acid fragments are partitioned, and then barcodes (e.g., barcodes linked to, or incorporated into, a solid or gel support) are subsequently added (e.g., by fusing, injection, microfluidics, or other means).

In some embodiments, cross-linked DNA product is digested with an endonuclease that produces fragments containing single-stranded sticky ends. In some cases, the fragments can be partitioned into partitions such that the partitions contain cross-linked DNA digest fragments and a solid or gel support (e.g., a bead such as an agarose bead) linked to, or associated with, one or more double-stranded barcode adaptor oligonucleotides. In some cases, the one or more double-stranded barcode adaptor oligonucleotides contain single-stranded sticky ends compatible with the sticky ends generated by the cross-linked DNA product endonuclease digestion. In some cases, the one or more double-stranded barcode adaptor oligonucleotides contain one or more priming sites for, e.g., PCR or sequencing. In some cases, the one or more double-stranded barcode adaptor oligonucleotides contain restriction sites such that the compatible sticky ends are generated by digestion in the partition(s). In some cases, the digest fragments of the cross-linked DNA product and the double-stranded barcode adaptor oligonucleotides are both generated by digestion in the partition(s). Double-stranded barcode adaptor oligonucleotides containing compatible sticky ends can be ligated to the cross-linked DNA digest fragments forming barcoded and cross-linked DNA digest fragments. The partitions can then be combined and the barcoded and cross-linked DNA digest fragments reverse cross-linked and then subject to one or more of the foregoing detection steps. Alternatively, the reverse cross-linking can be performed before digestion but after partitioning, before ligation of double-stranded barcode adaptor oligonucleotides, and/or before combining of the partitions. In yet another alternative, the cross-linked DNA products are not reverse cross-linked.

In an alternate embodiment, cross-linked DNA is digested or sheared and partitioned into partitions such that the partitions contain cross-linked DNA fragments (e.g., digested or sheared) and a solid or gel support (e.g., a bead such as an agarose bead) linked to, or associated with, one or more barcoded adaptor oligonucleotides containing a random primer sequence. Exemplary random primer sequence include, but are not limited to random pentamers, hexamers, septamers, octomers, nonamers, decamers, etc. Alternatively, the barcoded adaptor oligonucleotides can contain a non-random primer sequence, such as the sequence of a genomic region of interest. The one or more barcoded adaptor oligonucleotides containing a primer sequence can then generate polymerization products containing the barcode sequence by hybridizing the barcoded adaptor oligonucleotides to the cross-linked DNA fragments and performing DNA polymerization. The partitions can then be combined and the barcoded and cross-linked DNA fragment polymerization products subject to one or more of the foregoing detection steps. In some cases, the cross-linked DNA fragments are reverse cross-linked before barcoding, after barcoding but before combining partitions, or after combining partitions. In some cases, the reverse cross-linking is performed during the generation of cross-linked DNA fragment polymerization products containing the barcode sequence by hybridizing the barcoded adaptor oligonucleotides to the cross-linked DNA fragments and performing DNA polymerization. In still other cases, reverse cross-linking is not performed.

In some cases, the barcodes are partitioned as double or single stranded oligonucleotides (e.g., DNA, RNA, or a combination thereof) incorporated into, or linked to, a solid or gel support. Methods and compositions for making and using solid or gel supports with linked or incorporated oligonucleotides include those described, e.g., in U.S. Provisional Patent Appl. No. 62/015,568. In some cases, after partitioning, the oligonucleotides are conjugated to cross-linked DNA fragments (e.g., by ligation and/or polymerization) and the solid or gel support is dissolved by heating. In some cases, after partitioning the solid or gel support is dissolved by heating and then the oligonucleotides containing the barcodes conjugated to cross-linked DNA fragments (e.g., by ligation and/or polymerization).

As described herein, the barcodes, e.g., barcodes linked to or incorporated into a solid or gel support, can be partitioned by fusing partitions containing the barcodes (and optionally the solid or gel supports) with partitions containing cross-linked DNA products. Alternatively, the barcodes, e.g., barcodes linked to or incorporated into a solid or gel support, can be partitioned by injecting the barcodes (and optionally the solid or gel supports) into partitions containing cross-linked DNA products. As yet another alternative, cross-linked DNA fragments can be delivered to barcode containing partitions (e.g., partitions containing barcodes oligonucleotides linked to, or incorporated into, solid or gel supports) by partitioning, fusion, injection, microfluidics, or other means.

III. Compositions

In some embodiments, a library of partitioned cross-linked DNA fragments is provided. In some embodiments, a library of partitioned reverse cross-linked DNA fragments is provided. The partitioned cross-linked or reverse cross-linked DNA fragments can be barcoded. In such cases, the partitioning can be virtual partitioning in that the fragments are not physically partitioned, but the barcodes provide partitioning information. In some cases, one or more of the foregoing libraries can be used to detect chromosome or chromatin conformation at one or more genomic regions. For example, two or more DNA sequence elements (e.g., sequence elements that are more than about 250 bp apart) can be detected in the partitions of one or more of the foregoing libraries to determine the frequency that the DNA sequence elements are in proximity. In some cases, the library can be used to probe chromosome or chromatin conformation at multiple genomic regions simultaneously or sequentially.

Partitioned cross-linked DNA fragment or reverse cross-linked DNA fragment libraries can be prepared using any of the methods described herein. Such libraries can be stored for future conformation capture analysis and/or analyzed immediately after preparation. In some cases, multiple libraries are prepared in which each library is prepared from cells that have been differentially treated. In some cases, the chromosome or chromatin conformation of the differentially treated cells can be compared to control (e.g., untreated or differentially treated) cells by comparing the conformation library form the treated cells with a control conformation library. Alternatively, libraries can be prepared from different cell types or cells from different tissues. In some embodiments, cells can be modified, such as by one or more genomic modifications, and conformation libraries prepared from the modified cells.

IV. Kits

Kits containing compositions, and optionally, instructions for carrying out methods of the present invention are provided. For example, a kit can contain primers and/or enzymes and instructions for cross-linking, digesting or shearing, partitioning, reverse cross-linking, or detecting one or more DNA sequence elements. In some cases, the kit can contain one or more of enzymes, buffers, salts, nucleotides, reagents for forming partition mixtures, and detection reagents.

IV. Examples

The following examples are provided by way of illustration only and not by way of limitation. Those of skill in the art will readily recognize a variety of non-critical parameters that could be changed or modified to yield essentially the same or similar results.

Example 1

Figure 1:
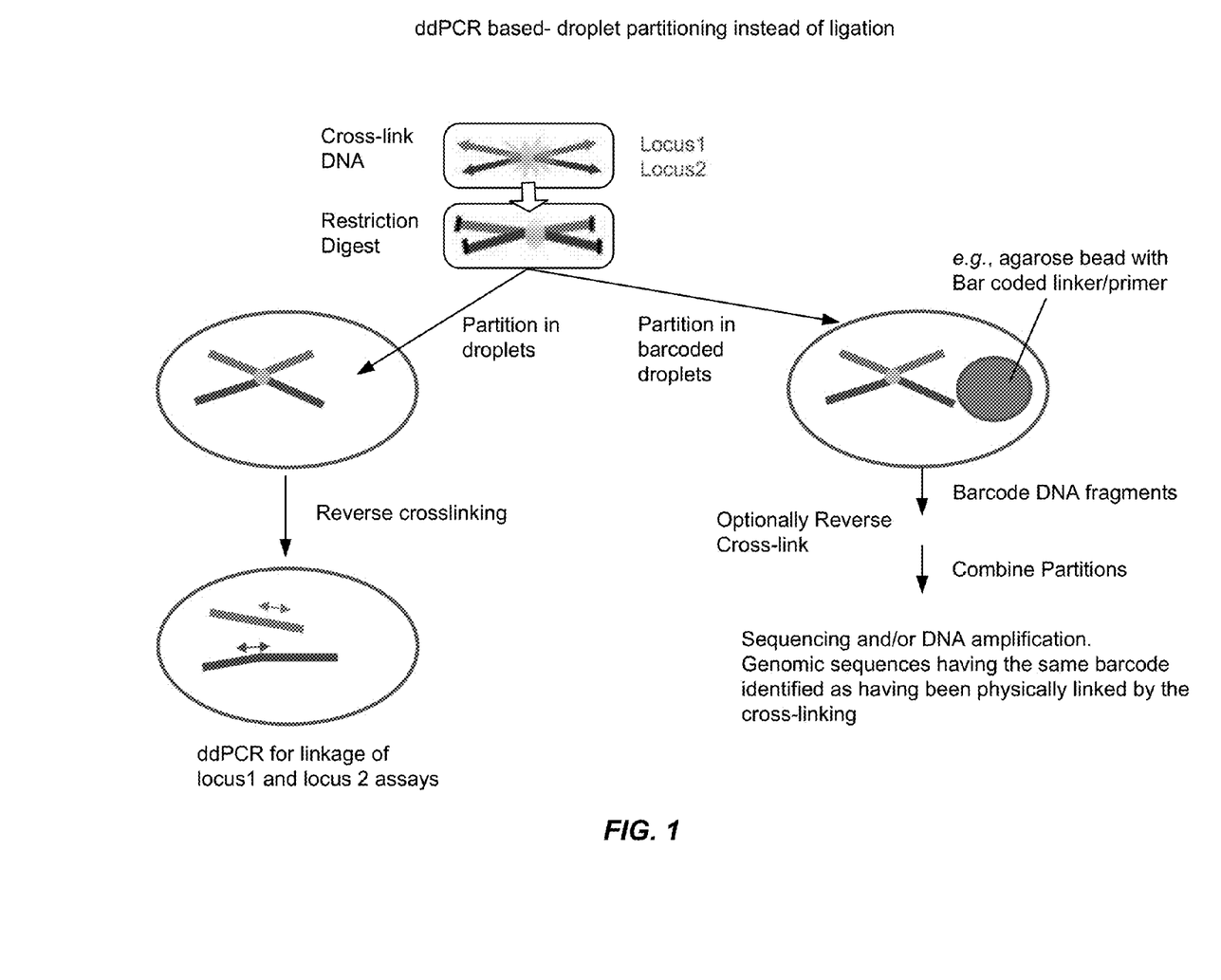
FIG. 1 depicts several embodiments of a method of performing partition-based chromosome capture analysis.
Figure 2:
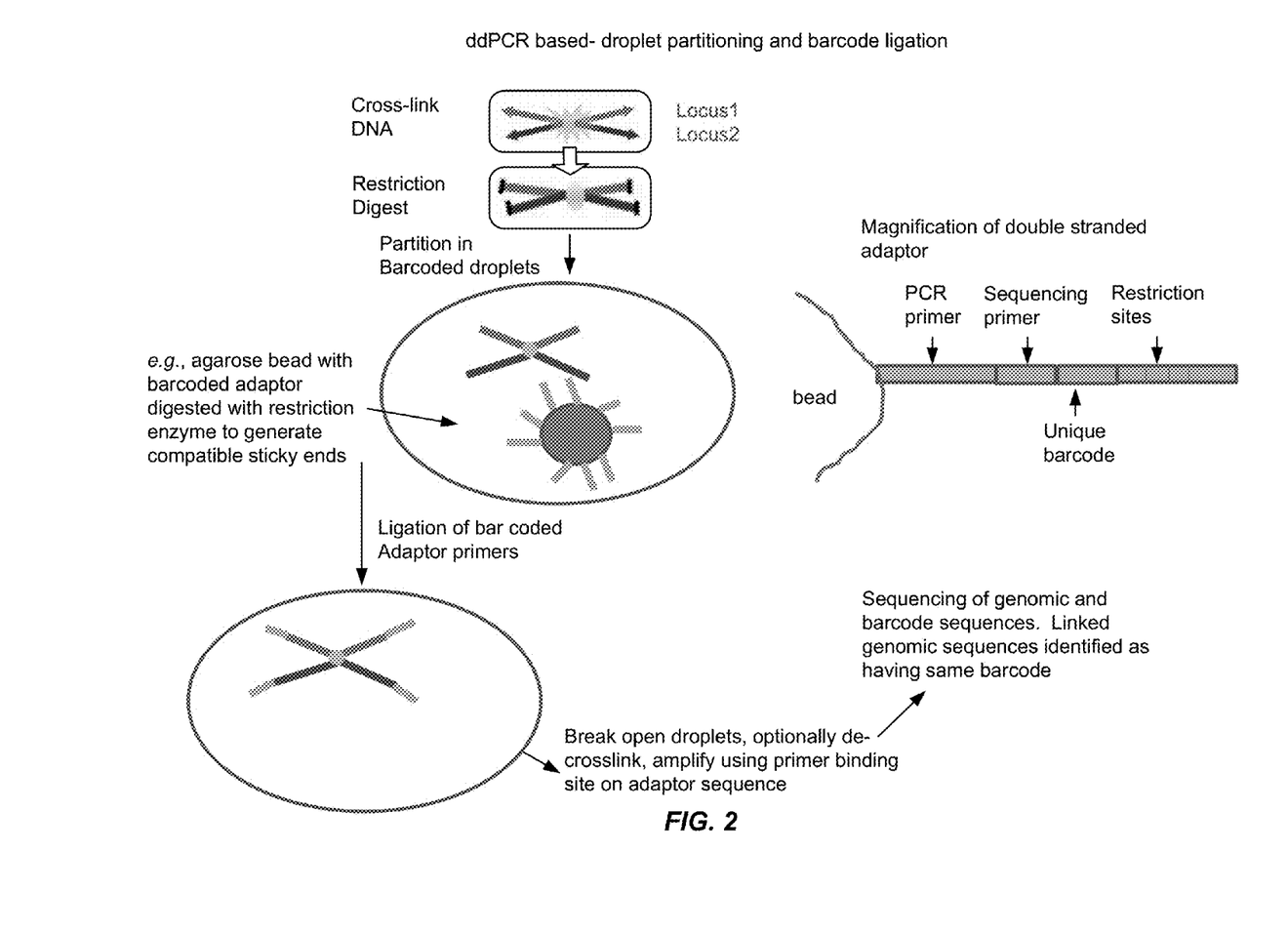
Figure 3:
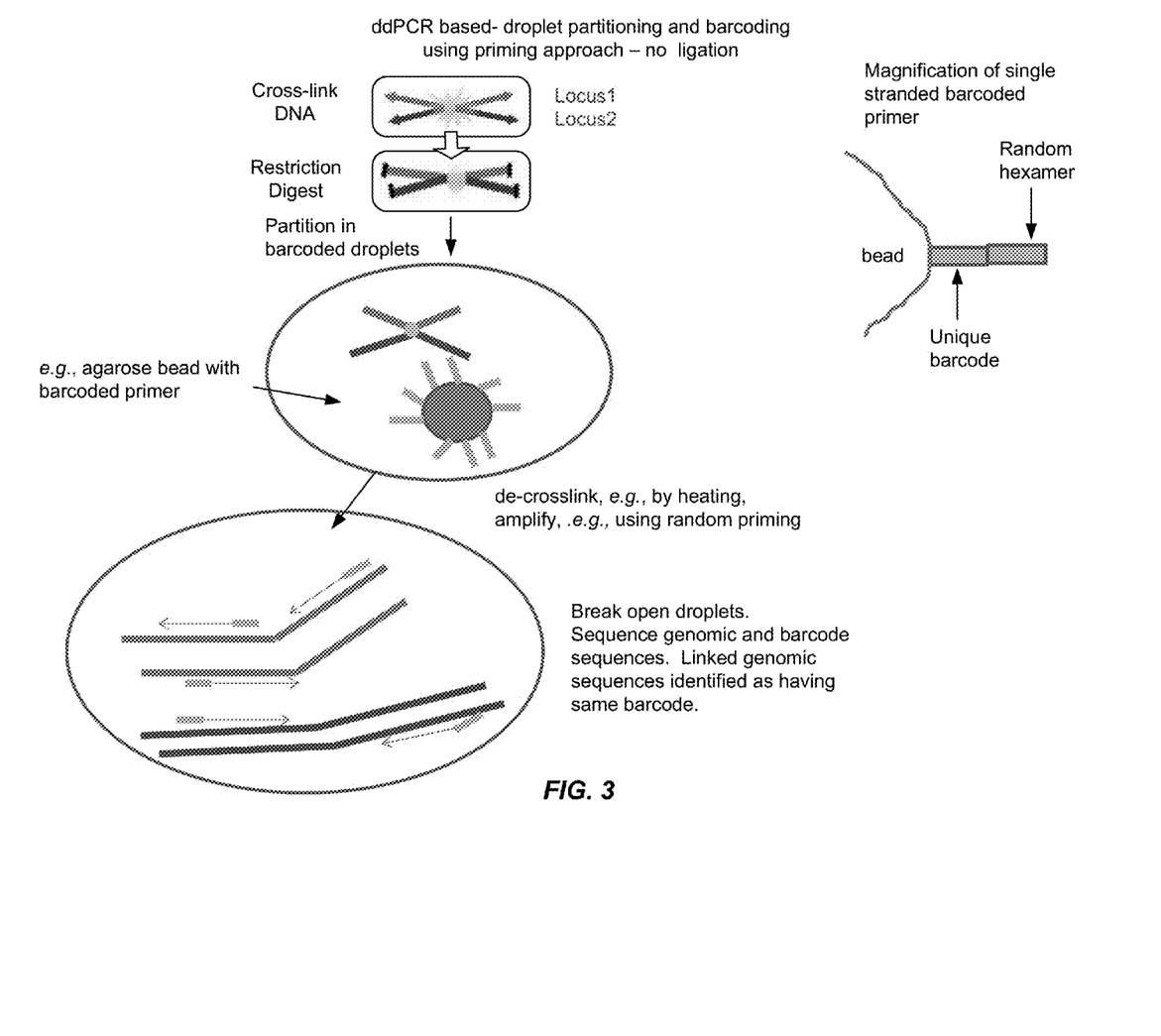
Figure 4:
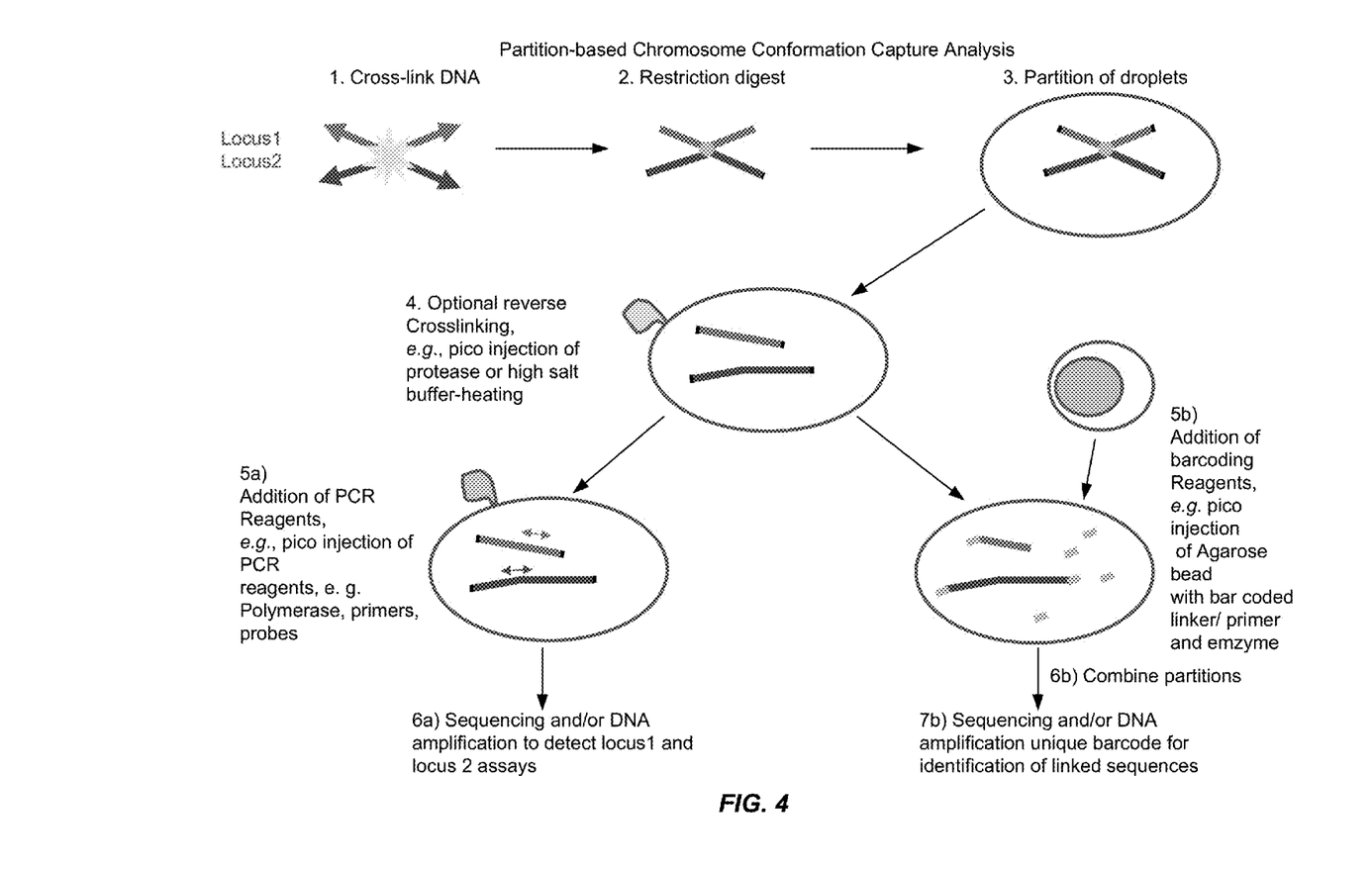
FIG. 4 depicts several embodiments of a method of performing partition-based chromosome capture analysis. In this embodiment, cross-linked DNA is partitioned, and additional reagents are injected into partitions at one or more downstream processing steps.

Chromatin is cross-linked using standard protocols and digested with a restriction enzyme. The resulting cross-linked DNA fragments are then diluted and partitioned into droplets containing a ddPCR assay reaction mix. Cross-linked fragments end up in same droplets. DNA is optionally reverse cross-linked in the initial denaturation step during ddPCR. Double positive droplets (i.e., droplets testing positive for two different DNA sequence elements) indicate that DNA sequence elements were cross-linked and thus physically connected in the chromatin state inside the cell. Thus, this method does not require ligation of cross-linked DNA before reverse cross-linking and eliminates artifacts caused by this ligation step. See, FIGS. 1-4.

Example 2

Chromatin is cross-linked using standard protocols and digested with a restriction enzyme. The resulting cross-linked DNA fragments are then diluted and partitioned into droplets containing a barcode. Cross-linked fragments end up in same droplets. Cross-linked DNA fragments are conjugated via ligation or polymerization to the barcodes. DNA is optionally reverse cross-linked. Droplets are combined, and the barcoded DNA is sequenced and/or amplified. DNA sequence elements having the same barcode are identified as having been physically linked during the cross-linking (e.g., in the chromatin state inside the cell). See, FIGS. 1-4.

Example 3

Chromatin is cross-linked using standard protocols and digested with a restriction enzyme. The resulting cross-linked DNA fragments are then diluted and partitioned into droplets. Cross-linked fragments end up in same droplets. Cross-linked DNA fragments are optionally reverse cross-linked by heating, injection of protease or high salt buffer, or a combination thereof. Barcoding reagents are injected into the droplets. Barcodes are conjugated to the DNA fragments via ligation or polymerization. Droplets are combined, and the barcoded DNA is sequenced and/or amplified. DNA sequence elements having the same barcode are identified as having been physically linked during the cross-linking (e.g., in the chromatin state inside the cell). See, FIG. 4, subsections 1-4, and 5b)-7b). Alternatively, ddPCR reagents are injected into the droplets and ddPCR performed. Double positive droplets (i.e., droplets testing positive for two different DNA sequence elements) indicate that DNA sequence elements were cross-linked and thus physically connected in the chromatin state inside the cell. See, FIG. 4, subsections 1-4, and 5a)-6a).

All patents, patent applications, and other publications, including GenBank Accession Numbers, cited in this application are incorporated by reference in the entirety for all purposes.

What is claimed is:

1. A method for detecting chromosomal DNA sequence elements that are in close proximity in a cell or in an intact nucleus, the method comprising:
   a) cross-linking the chromosomal DNA in the cell or the intact nucleus, thereby forming a cross-linked DNA product in which chromosomal DNA sequence elements that are in close proximity in the cell or the intact nucleus are cross-linked;
   b) obtaining the cross-linked DNA product;
   c) digesting the cross-linked DNA product with an endonuclease to form a mixture containing a plurality of cross-linked DNA digest fragments;
   d) partitioning the cross-linked DNA digest fragments to create a plurality of partitions, wherein the partitions are droplets; and
   e) detecting the presence of two or more DNA sequence elements that are distal with respect to the primary sequence of the genome in a single droplet partition, wherein detection of two or more DNA sequence elements in a single droplet partition indicates that the two or more DNA sequence elements were in close proximity in the cell or intact nucleus.

2. The method of claim 1, wherein the cross-linked DNA digest fragments are partitioned such that the average number of cross-linked DNA digest fragments in each droplet partition is about 1 or less.

3. The method of claim 1, further comprising, after the step of digesting the cross-linked DNA, reversing the cross-linking, thereby generating two reverse-cross-linked-DNA digest fragments from the cross-linked DNA digest fragment in the droplet partitions.

4. The method of claim 3, wherein the detecting comprises detecting reverse-cross-linked DNA digest fragments in the droplet partitions, wherein detection of two reverse-cross-linked DNA digest fragments in a single droplet partition indicates that the two reverse-cross-linked DNA digest fragments were cross-linked, thereby detecting chromosomal DNA sequence elements that were in close proximity in the cell or intact nucleus.

5. The method of claim 1, wherein all, substantially all, or a portion of the plurality of droplet partitions contain a nucleic acid barcode.

6. The method of claim 5, wherein the nucleic acid barcode is linked to a solid support.

7. The method of claim 1, wherein the detection comprises DNA amplification.

8. The method of claim 1, wherein the detection step comprises nucleic acid sequencing.

9. The method of claim 1, wherein the cross-linking the chromosomal DNA in the intact nucleus comprises incubating a cell with a cross-linking agent.

10. The method of claim 1, wherein the cross-linking the chromosomal DNA in the intact nucleus comprises incubating a purified intact nucleus with a cross-linking agent.

11. A method for detecting chromosomal DNA sequence elements that are in close proximity in a population of intact nuclei, the method comprising performing the method of claim 1 on a plurality of intact nuclei.

12. The method of claim 11, wherein the method further comprises quantitating the frequency of cross-linking of two or more DNA sequence elements, thereby quantitating the frequency that the two or more DNA sequence elements are in close proximity in the population of intact nuclei.

13. The method of claim 1, wherein the partitioning the cross-linked DNA digest fragments to create a plurality of partitions comprises creating at least 10,000 droplet partitions.

14. The method of claim 1, wherein the droplet partitions are less than about 100 nL in volume.

15. A method for detecting nucleic acid sequence elements that are in close proximity in a cell or in an intact nucleus, the method comprising:
   a) cross-linking chromosomal DNA in the cell or the intact nucleus, thereby forming a cross-linked DNA product containing DNA and RNA, wherein nucleic acid sequence elements that are in close proximity in the cell or the intact nucleus are cross-linked;
   b) obtaining the cross-linked DNA product;
   c) digesting the cross-linked DNA product with an endonuclease to form a mixture containing a plurality of cross-linked DNA digest fragments;
   d) partitioning the cross-linked DNA digest fragments to create a plurality of partitions, wherein the partitions are droplets; and
   e) detecting the presence of two or more nucleic acid sequence elements that are distal with respect to the primary sequence of the genome in a single droplet partition, wherein detection of two or more nucleic acid sequence elements in a single droplet partition indicates that the two or more nucleic acid sequence elements were in close proximity in the cell or intact nucleus.

16. The method of claim 15, wherein the method further comprises reverse transcribing the RNA in the cross-linked DNA product.

* * * * *

UNITED STATES PATENT AND TRADEMARK OFFICE
CERTIFICATE OF CORRECTION

PATENT NO. : 9,822,396 B2  
APPLICATION NO. : 14/622515  
DATED : November 21, 2017  
INVENTOR(S) : Claudia Litterst, Svilen Tzonev and Jeremy Agresti

Page 1 of 1

It is certified that error appears in the above-identified patent and that said Letters Patent is hereby corrected as shown below:

On the Title Page

Item (73) Assignees:
"Bio-Rad Laboratories, Inc.; Hercules, Inc."
Should read:
--Bio-Rad Laboratories, Inc.; Hercules, CA--

Signed and Sealed this
Twentieth Day of November, 2018

Andrei Iancu
*Director of the United States Patent and Trademark Office*